(12) United States Patent
Malvestiti et al.

(10) Patent No.: US 9,708,263 B2
(45) Date of Patent: Jul. 18, 2017

(54) SYNTHESIS OF AN AZASUGAR AND THE INTERMEDIATES THEREOF

(71) Applicant: DIPHARMA FRANCIS s.r.l., Baranzate (IT)

(72) Inventors: Andrea Malvestiti, Baranzate (IT); Enrico Brunoldi, Baranzate (IT); Emanuele Attolino, Baranzate (IT)

(73) Assignee: Dipharma Francis S.r.l., Baranzata (IT)

( * ) Notice: Subject to any disclaimer, the term of this patent is extended or adjusted under 35 U.S.C. 154(b) by 0 days.

(21) Appl. No.: 15/098,647

(22) Filed: Apr. 14, 2016

(65) Prior Publication Data
US 2016/0304458 A1    Oct. 20, 2016

(30) Foreign Application Priority Data

Apr. 17, 2015   (IT) .................. 102015000012245

(51) Int. Cl.
*C07D 211/46*   (2006.01)

(52) U.S. Cl.
CPC .................. *C07D 211/46* (2013.01)

(58) Field of Classification Search
CPC ................................... C07D 211/46
USPC .......................................... 546/243
See application file for complete search history.

(56) References Cited

U.S. PATENT DOCUMENTS

| 4,639,436 A | 1/1987 | Junge et al. |
| 8,802,155 B1 | 8/2014 | Attolino et al. |
| 2014/0243369 A1 | 8/2014 | Attolino et al. |

FOREIGN PATENT DOCUMENTS

| EP | 000947 A1 | 3/1979 |
| EP | 00 55 431 A1 | 7/1982 |
| EP | 0 367 748 A2 | 9/1990 |

OTHER PUBLICATIONS

Dorwald, Side Reactions in Organic Synthesis, 2005, Wiley: VCH Weinheim Preface, pp. 1-15 & Chapter 8, pp. 279-308.*
Carlos R.R. Matos et al., Synthesis of 1-Deoxynojirimycin and N-Butyl-1-deoxynojirimycin, Synthesis, vol. 1999, 571-573.
Baxter et al., "Expeditious Synthesis of Azasugars by the Double Reductive Amination of Dicarbonyl Sugars", J. Org. Chem. 1994, 59, 3175-3185.
Wennekes et al., "Large-Scale Synthesis of the Glucosylceramide Synthase Inhibitor N-[5-(Adamantan-1-yl-methoxy)-pentyl]-1-deoxynojirimycin", Organic Process Research & Development 2008, 12, 414-423.
Paulsen et al., Synthese and Reaktionen von Keto-piperidinosen, Chem. Ber. 1967, 100, 802-815.
Schitter et al., "Synthesis of lipophilic 1-deoxygalactonojirimycin derivatives as D-galactosidase inhibitors", Beilstein Journal of Organic Chemistry, vol. 6, Mar. 1, 2010.
Italian Search Report issued in ITUB20150176 dated Jul. 28, 2015, 8 pages.

* cited by examiner

*Primary Examiner* — Patricia L Morris
(74) *Attorney, Agent, or Firm* — Rothwell, Figg, Ernst & Manbeck, P.C.

(57) ABSTRACT

Process for the preparation of intermediates useful in the synthesis of miglustat and their use in its manufacture.

17 Claims, No Drawings

SYNTHESIS OF AN AZASUGAR AND THE INTERMEDIATES THEREOF

The present invention relates to a process for the preparation of intermediates useful in the synthesis of miglustat, an active ingredient having known activity as a glycosyltransferase inhibitor, and their use in its manufacture.

PRIOR ART

N-butyl 1,5-dideoxy-1,5-imino-d-glucitol of formula (I), also known as N-butyl 1-deoxynojirimycin or miglustat, is a potent glycosyltransferase inhibitor, primarily used in the treatment of Gaucher's disease.

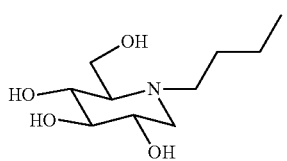

Miglustat belongs to the class of azasugars or iminosugars, compounds with multiple biological activities, characterised by the presence of a nitrogen atom on the furanose or pyranose ring of the sugar instead of an oxygen atom. The synthesis of azasugars as carbohydrate mimics began over 50 years ago. The first azasugar synthesized by Paulsen (*Chem. Ber.* 1967, 100, 802) was 1-deoxynojirimycin of formula (II), which was isolated from natural sources only years later, and demonstrated its enormous biological activity.

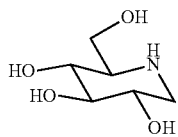

In the 1980s, a number of studies conducted on the biological activity of N-alkylated derivatives of 1-deoxynojirimycin of formula (II) demonstrated that said compounds possess a greater activity than 1-deoxynojirimycin, and the N-butyl derivative of formula (I) proved to be one of the best. As it was a synthetic derivative of 1-deoxynojirimycin, the first syntheses of miglustat were obviously conducted by introducing the butyl chain onto 1-deoxynojirimycin of formula (II), or derivatives thereof with the functional groups protected, by reductive amination with butyraldehyde (see, for example, U.S. Pat. No. 4,639,436 and EP 367748).

Said syntheses obviously shifted the synthesis problem of preparation of the N-alkylated derivative to the efficient synthesis of 1-deoxynojirimycin which, though present in nature in numerous plants and micro-organisms, cannot be extracted in sufficient quantities to allow its industrial exploitation, but must be prepared by chemical synthesis. Various methods of preparation of 1-deoxynojirimycin have been reported over the years, some of them completely chemical or biochemical with the aid of more or less complex micro-organisms, normally starting with sugars such as glucose and ribose. An interesting synthesis of N-alkylated derivatives of 1-deoxynojirimycin, including miglustat, was published by Baxter and Reitz in *J. Org. Chem.* 1994, 59, 3175-3185. Its synthesis uses one of the classic methods of preparing piperidine and pyrrolidine, namely double reductive amination of 1,5-dicarbonyl derivatives with primary amines.

Several of the problems of said preparation have been partly eliminated with time, due to the synthesis reported by Matos C. R. R. et al. (*Synthesis* 1999, 571-573), which involves forming miglustat of formula (I) by debenzylating the key protected intermediate of formula (III) (Scheme 1)

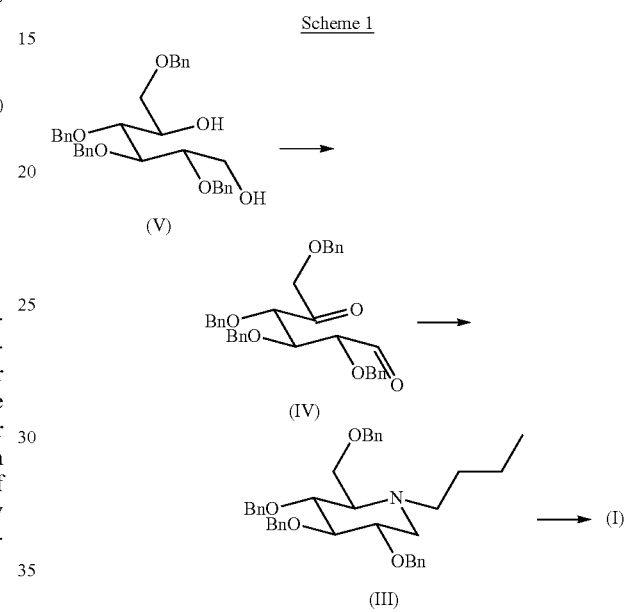

obtained from the protected dicarbonyl of formula (IV). This can be prepared with good yields, without the use of the tin derivatives reported by Baxter, from 2,3,4,6-tetra-O-benzyl-d-glucitol of formula (V), which can be prepared by reducing commercially available 2,3,4,6-tetra-O-benzyl-D-glucose which, in turn, can be prepared from D-glucose by known methods.

The preparation of the dicarbonyl of formula (IV) starting with the diol of formula (V) was subsequently improved by Wennekes et al., in *Organic Process Research & Development* 2008, 12, 414-423, especially with a view to developing a process suitable for use on an industrial scale.

However, the Wennekes procedure does not solve yet another problem connected with the use of NaCNBH$_3$ in the step involving double reductive amination of dicarbonyl (IV) with butylamine. Since Baxter's discovery of the method in 1994, no one else has reported a different reducing agent for performing reductive amination. NaCNBH$_3$ is used in excess in the reaction (4 moles of reducing agent per mole of starting diol (V)), and in each manipulation, the authors emphasise the need to take important precautions to prevent the release of the toxic, hazardous HCN. The work-up of the reaction is also performed at basic pH values to ensure that the cyanide ions goes into the aqueous phase. Given the scientific nature of Wennekes' study, it obviously does not report on the disposal of wastewater containing cyanide ions, but from the industrial standpoint this is a major problem that needs to be eliminated if the process is to be industrially scalable. The authors of the present invention attempted to conduct the same reductive amination reaction as reported by Wennekes starting with the dicarbonyl of formula (IV), using the safer NaBH$_4$, NaBH(OAc)$_3$ or Pd/C and H$_2$ as reducing agent, but in all cases the end-of-reaction crude substance proved not to contain the desired product.

There is consequently a need for a reducing process and a reducing agent to prepare a compound of formula (III), and therefore miglustat of formula (I), which eliminates all the drawbacks reported above, and enables the desired product to be obtained efficiently, on an industrial scale, so that it is harmless to humans and environment-friendly, by a simple method providing high yields and purity.

SUMMARY OF THE INVENTION

The invention provides a process for the preparation of a compound of formula (VI) or a salt thereof

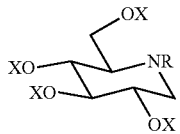

(VI)

wherein X is H or an alcohol-protecting group; and R is H, a C$_1$-C$_6$ alkyl group, or an amino-protecting group; comprising the double reductive amination reaction of a dicarbonyl compound of formula (VII), wherein X is as defined above,

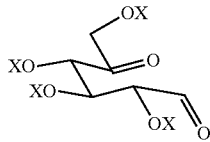

(VII)

with an amine of formula (VIII) or a salt thereof

NH$_2$—R          (VIII)

wherein R is as defined above, in the presence of a borane complex with an amine of formula (IX) or a borane complex with a pyridine of formula (X), as defined herein. According to the process to which the invention relates, a compound of formula (VI), wherein X is H and R is butyl, is already miglustat of formula (I); moreover, a compound of formula (VI), wherein the substituents X and R, being as defined herein, have values other than H and butyl respectively, can be used in the synthesis of miglustat of formula (I).

DETAILED DESCRIPTION OF THE INVENTION

The subject of the present invention is a process for the preparation of a compound of formula (VI) or a salt thereof

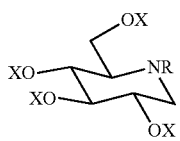

(VI)

wherein X is H or an alcohol-protecting group; and R is H, an optionally substituted C$_1$-C$_6$ alkyl group, or an amino-protecting group; comprising the double reductive amination reaction of a dicarbonyl compound of formula (VII), wherein X is as defined above,

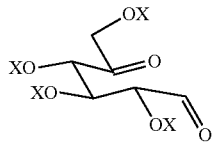

(VII)

with an amine of formula (VIII) or a salt thereof

NH$_2$—R          (VIII)

wherein R is as defined above, in the presence of a reducing agent selected from a borane complex with an amine of formula (IX) or a borane complex with a pyridine of formula (X)

BH$_3$·NY$_3$,          (IX)

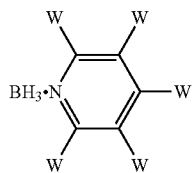

(X)

wherein each of the substituents Y, being the same or different, is H, an optionally substituted C$_1$-C$_6$ alkyl or aryl group, or two of Y, taken together with the nitrogen atom to which they are linked, form a C$_5$-C$_6$ cycloalkyl ring optionally containing an oxygen atom or an =NRa group, wherein Ra is hydrogen, an amino-protecting group, or a C$_1$-C$_4$ alkyl group; and each of the substituents W, which are the same or different, is H, an optionally substituted C$_1$-C$_6$ alkyl group, or a halogen atom; and of a solvent and, if the case, the conversion of a compound of formula (VI) to another compound of formula (VI) or a salt thereof, or the conversion of a salt of a compound of formula (VI) to its free base, or the conversion of a compound of formula (VI) into salt thereof.

A salt of a compound of formula (VI) or (VIII) is typically a pharmaceutically acceptable salt.

R as amino-protecting group is, for example, an amino-protecting group known from the chemistry of peptides, such as a group selected from benzyl, benzyloxycarbonyl, tert-butyloxycarbonyl, 9-fluorenylmethyl, 2-chloro-3-indenylmethyl, 2,2,2-trichloroethyl, 2-chloroethyl, 2-adamantyl, 8-quinolyl, 4-methylsulfinylbenzyl, 2-metylthioethyl, 4-azidobenzyl, and N'-phenylaminothiocarbonyl, preferably benzyl.

In an amine of formula (VIII), or a salt thereof, R is preferably butyl.

X as alcohol-protecting group is, for example, an alcohol-protecting group known from carbohydrate chemistry, for instance a group selected from a lower alkanoyl, such as formyl, acetyl, chloroacetyl, trifluooacetyl, or benzoyl; allyl; propargyl; or for example a substituted phenyl ether, such as benzyl and substituted benzyl, such as p-methoxybenzyl, p-halobenzyl, e.g. p-bromobenzyl or 2,6-dichlorobenzyl; and a silylether type, such as tri-lower alkylsilyl, e.g. trimethylsilyl; preferably benzyl.

A C$_1$-C$_6$ alkyl group, which may be straight or branched, is typically a C$_1$-C$_4$ alkyl group such as methyl, ethyl, propyl, isopropyl or butyl, isobutyl, tert-butyl, which can be substituted by one or more substituents, which are equal or different, preferably by one to three substituents, such as hydroxyl or halogen, in particular chlorine or fluorine.

An aryl group can, for example, be a phenyl group optionally substituted by one to three substituents, which may be the same or different, selected independently from a straight or branched $C_1$-$C_4$ alkyl group, which in turn is optionally substituted by one to three halogen atoms, typically fluorine; a hydroxy group; a $C_1$-$C_4$ alkoxy group, for example methoxy; a halogen atom, such as bromine or chlorine; a cyano group; and a nitro group.

A reducing agent is preferably selected from a borane complex with an amine of formula (IX) or a borane complex with a pyridine of formula (X), wherein in the amine $NY_3$ preferably one or two of Y, which may be the same or different, is a $C_1$-$C_4$ alkyl group, more preferably methyl, ethyl or t-butyl, the remaining one or two of Y being hydrogen; or two of Y, taken together with the nitrogen atom to which they are linked, form a $C_5$-$C_6$ cycloalkyl ring, optionally containing an oxygen atom or an =NRa group, wherein Ra is hydrogen, an amino-protecting group or a $C_1$-$C_4$ alkyl group, the remaining one of Y being hydrogen; and in the borane complex with a pyridine of formula (X), the pyridine ring is unsubstituted or typically substituted by one to three substituents independently chosen from a halogen atom and a $C_1$-$C_6$ alkyl group.

A $C_5$-$C_6$ cycloalkyl ring is preferably a piperidine.

A $C_5$-$C_6$ cycloalkyl ring containing an oxygen atom is preferably a morpholine ring.

A $C_5$-$C_6$ cycloalkyl ring containing an =NRa group is preferably a piperazine ring, wherein Ra is hydrogen, an amino-protecting group, or a $C_1$-$C_4$ alkyl group, preferably methyl, ethyl or propyl.

A substituted pyridine ring is preferably substituted by one, two or three substituents independently selected from a halogen atom, typically chlorine, preferably in the 2 position of the pyridine ring, and a $C_1$-$C_6$ alkyl group, preferably selected independently from methyl, ethyl and propyl, preferably in the 2 and 5 positions of the pyridine ring.

A reducing agent is preferably selected from a borane complex with an amine of formula (IX) or a borane complex with a pyridine of formula (X), wherein in the amine $NY_3$ preferably one or two of Y, which may be the same or different, is a $C_1$-$C_4$ alkyl group, more preferably methyl, ethyl or t-butyl, the remaining one or two of Y being hydrogen; or two of Y, taken together with the nitrogen atom to which they are linked, form a morpholine, piperidine or piperazine ring, the remaining one of Y being hydrogen; and in the borane complex with a pyridine of formula (X), the pyridine ring is unsubstituted or typically substituted by one or two $C_1$-$C_4$ alkyl groups, which may be the same or different, more preferably selected independently from methyl, ethyl and propyl.

In a borane complex with an amine of formula (IX), one or two of Y is preferably a $C_1$-$C_4$ alkyl group, preferably selected from methyl and t-butyl, which may be the same or different, the remaining one or two of Y being hydrogen; or two of Y, taken together with the nitrogen atom to which they are linked, form morpholine, piperidine or piperazine ring, the remaining one of Y being hydrogen.

In a borane complex with a pyridine of formula (X), the pyridine ring is preferably substituted by one or two $C_1$-$C_6$ alkyl groups, which may be the same or different, preferably by one or two $C_1$-$C_4$ alkyl groups, more preferably selected independently from methyl, ethyl and propyl.

The reductive amination reaction can be carried out by treating a dicarbonyl compound of formula (VII) with at least a stoichiometric amount of amine of formula (VIII) and at least 2 moles of reducing agent of formula (IX) or (X) per mole of compound of formula (VII).

The reductive amination reaction can be advantageously carried out at a reaction temperature ranging between about 0° C. and about 30° C., preferably at about 25° C., the pH of the reaction mixture typically ranging between about 8 and about 4.

The pH value of the reaction mixture can be suitably controlled by adding acetic acid to the reaction mixture.

The reductive amination reaction can optionally be carried in the presence of a solvent, selected, for example, from a dipolar aprotic solvent, typically dimethylformamide, dimethylacetamide, acetonitrile or dimethylsulphoxide; an ether, typically tetrahydrofuran or dioxane or methyl-tert-butyl ether; a chlorinated solvent, typically dichloromethane; an apolar solvent, typically toluene or hexane; an ester, such as ethyl acetate, isopropyl acetate or butyl acetate; a polar protic solvent, typically a $C_1$-$C_4$ alkanol, preferably methanol, or water, or a mixture of two or more, preferably two or three, of said solvents.

A compound of formula (VI) can be converted to another compound of formula (VI), or a salt thereof, by known methods; and similarly, a salt thereof can be converted to its free base or a compound of formula (VI) can be converted to a salt thereof.

For example, a compound of formula (VI), wherein R is hydrogen and each of X is an alcohol-protecting group, can be alkylated, for example by known methods, to obtain a corresponding compound of formula (VI), wherein R is a $C_1$-$C_6$ alkyl group, in particular butyl, and then, by subsequent deprotection of the hydroxyl groups, converted to a corresponding compound of formula (VI), wherein each of X is hydrogen, and R is a $C_1$-$C_6$ alkyl group, in particular butyl, that is miglustat.

A compound of formula (VI), wherein R is a $C_1$-$C_6$ alkyl group, in particular butyl, and each of X is an alcohol-protecting group, in particular benzyl, can be converted to another compound of formula (VI), wherein each of X is hydrogen and R is a $C_1$-$C_6$ alkyl group, in particular butyl, namely miglustat, by removing the protecting groups according to known methods.

A compound of formula (VII) is known or can be obtained by known methods. For example, a compound of formula (VII), wherein X is benzyl, is a compound of formula (IV), reported above, and can be prepared by oxidation of 2,3,4, 6-tetra-O-benzyl-D-glucitol of formula (V) reported above, for example as described by Wennekes et al. in *Organic Process Research & Development* 2008, 12, 414-423.

The reducing agents of formula (IX) or (X) are commercially available.

Alternatively, they can be prepared in situ from a borane solution, complexed with THF or Me$_2$S, by treatment with a corresponding amine of formula (IXa) or a corresponding pyridine of formula (Xa), wherein Y and W are as defined above.

$$NY_3 \quad (IXa)$$

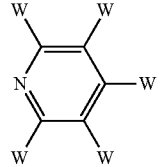

(Xa)

A solution of borane complexed with THF or Me$_2$S is commercially available or can also be prepared in situ by known methods.

In a more preferred aspect of the invention, the reducing agent used for the double reductive amination reaction is a borane complex with an amine of formula (IX), wherein the corresponding amine of formula (IXa) is a secondary amine, more preferably an amine of formula (IXa), wherein one Y group is H and the remaining two Y groups, taken together with the nitrogen atom to which they are bonded, form a morpholine ring. Said reducing agent is preferably prepared in situ.

A compound of formula (VI), thus obtained, can be isolated from the end-of-reaction environment after conventional aqueous washes and extraction in a solvent by methods known to the skilled person. A compound of formula (VI), extracted after aqueous washings from the reaction medium, is preferably purified by crystallisation, optionally after conversion to a pharmaceutically acceptable salt thereof.

The use of a reducing agent selected from a borane complex with an amine of formula (IX) or complex with a pyridine of formula (X), as defined above, is extremely efficient, economical and safe, and therefore advantageously usable on an industrial scale. Similarly, both the recovery of the product from the reaction mixture and the disposal of the wastewater is considerably simplified compared with the known methods for the double reductive amination reaction of the compound of formula (VII).

A compound of formula (VI) obtained by the process according to the present invention can be used to synthesize miglustat of formula (I) or, if X is H and R is butyl, a compound of formula (VI) is already miglustat.

The subject of the present invention is therefore a process for the preparation of miglustat of formula (I) comprising the use of a compound of formula (VI), obtained by the process according to the present invention.

The following examples further illustrate the invention.

Example 1

Synthesis of 2,3,4,6-tetra-O-benzyl-D-xylo-hexos-5-ulose of Formula (VII)

Oxalyl chloride (36 g, 0.29 mol) is dissolved in dichloromethane (120 ml) in a 500 ml reactor, and the solution is cooled to −65° C. A solution of DMSO (31 g, 0.40 mol) in dichloromethane (40 ml) and a solution of 2,3,4,6-tetra-O-benzyl-D-glucitol of formula (V) (41 g, 0.74 mol) in dichloromethane (40 ml) are then sequentially dripped slowly into the solution. At the end of the addition the reaction mixture is left under stirring for 30 minutes, and triethylamine (75 g, 0.74 mol) is then dripped into the mixture. The mixture is left to stand at 0° C. and treated with a 5.5% W/W solution of NaOCl (540 ml), maintaining the temperature below 5° C. The phases are separated and the organic phase is washed sequentially at 0° C. with distilled H$_2$O (200 ml) and 3M HCl (200 ml). The solution of 2,3,4,6-tetra-O-benzyl-D-xylo-hexos-5-ulose is used "as is" in the next step.

Example 2

Synthesis of 2,3,4,6-tetra-O-benzyl-N-butyl-1-deoxynojirimycin of Formula (VI)

A mixture of MeOH (40 ml), AcOH (15 g, 251 mol), n-butylamine (13.2 g, 181 mol) and Na$_2$SO$_4$ (3.2 g, 50 mmol) is prepared at 0° C. in a 250 ml reactor under N$_2$. The solution of the compound of formula (VII), prepared as described in Example 1 from 10 g of glucitol of formula (V), is dripped into the suspension, and at the end of the addition, solid borane morpholine (5.0 g, 47 mmol) is added. The reaction mixture is maintained at 0° C. for 3 h, and then left to stand at about 22-25° C. When the reaction has concluded, the end-of-reaction mixture is treated with a solution of 3M HCl (40 ml) and the development of gas is left to terminate; the phases are then separated, and the organic phase is washed sequentially with a 10% W/W solution of K$_2$CO$_3$ and a 5% W/W solution of NaCl. The phases are separated and the organic phase is dried on Na$_2$SO$_4$, filtered and evaporated at low pressure. 10.8 g of crude product is obtained, and purified by crystallisation from isopropanol. The resulting solid is filtered, washed with isopropanol and stove-dried at 50° C. under vacuum to a constant weight. 7.0 g of 2,3,4,6-tetra-O-benzyl-N-butyl-1-deoxynojirimycin is obtained as a white solid with a yield of 67%.

Example 3

Synthesis of 2,3,4,6-tetra-O-benzyl-N-butyl-1-deoxynojirimycin of Formula (VI)

NaBH$_4$ (3.85 g, 97 mmol) is suspended in THF (20 ml) in a 500 ml reactor under N$_2$, and morpholine (9.3 g, 106 mmol) is added. The suspension is cooled to 0° C. and a solution of I$_2$ (12.3 g, 48 mmol) in THF (20 ml) is dripped into it. At the end of dripping the reaction mixture is left to stand at room temperature until the development of gas has concluded. n-butylamine (27.2 g, 372 mmol) followed by MeOH (40 ml) is then dripped into the mixture. When the development of gas has ended, Na$_2$SO$_4$ (6.7 g, 104 mmol) and acetic acid (31.2 g, 520 mmol) are added. The mixture is cooled to 0° C. and a dichloromethane solution (200 ml) of 2,3,4,6-tetra-O-benzyl-D-xylo-hexos-5-ulose, prepared from 20 g of glucitol of formula (V) as described in Example 1, is dripped into it. The reaction mixture is maintained at 0° C. for 3 h, and then left to stand at about 22-25° C. When the reaction has concluded, the end-of-reaction mixture is washed with a 3M HCl solution, and when gas development is complete the phases are separated and the organic phase is washed sequentially with a 10% W/W solution of K$_2$CO$_3$ and a 5% W/W solution of NaCl. The organic phase is dried on Na$_2$SO$_4$, filtered and concentrated at low pressure. The product thus obtained is purified by crystallisation from isopropanol. The solid obtained is filtered, washed with isopropanol and stove-dried at 50° C. under vacuum. 12.2 g of 2,3,4,6-tetra-O-benzyl-N-butyl-1-deoxynojirimycin of formula (VI) is obtained as a white solid with a yield of 57%, starting from 2,3,4,6-tetra-O-benzyl-D-glucitol of formula (V), with a chemical purity, evaluated by HPLC, of 99.7% in A %.

Example 4

Synthesis of 2,3,4,6-tetra-O-benzyl-N-butyl-1-deoxynojirimycin of Formula (VI)

2,3,4,6-tetra-O-benzyl-D-glucitol of formula (V) (21.2 g, 37.0 mmol) is dissolved in DMSO (100 ml) in a 500 ml reactor under N$_2$ at 18° C. The solution is then treated with P$_2$O$_5$ (20.9 g, 147.5 mmol), added solid in portions, maintaining the temperature below 23° C. The reaction mixture is maintained under stirring for 1 h and then treated with triethylamine (23.1 g, 228.6 mmol). The mixture is diluted with toluene (100 ml), and demineralised H$_2$O (100 ml) is slowly dripped into it, maintaining the temperature below 25° C. The phases are separated and the organic phase is treated at 0° C., first with a 5.5% W/W aqueous solution of NaOCl, and then with an aqueous solution of NaCl. The solution containing the dicarbonyl of formula (VII) is then dripped into a 500 ml reactor at 0° C. containing the reducing system prepared by the procedure described in Example 3 starting with NaBH$_4$ (3.85 g, 97 mmol), THF (20 ml), morpholine (9.3 g, 106 mmol), a solution of I$_2$ (12.3 g, 48 mmol) in THF (20 ml), n-butylamine (27.2 g, 372 mmol), MeOH (40 ml), Na$_2$SO$_4$ (6.7 g, 104 mmol) and acetic acid (31.2 g, 520 mmol) At the end of the addition the reaction mixture is maintained at 0° C. for 3 h and then left to stand at room temperature. When the reaction has concluded, the end-of-reaction mixture is treated with a 3M HCl solution, and the development of gas is left to complete. The phases are separated and the organic phase is washed sequentially with a 10% W/W solution of K$_2$CO$_3$ and a 5% W/W solution of NaCl. The organic phase is then dried on Na$_2$SO$_4$, filtered, and concentrated at low pressure. The residue obtained is purified by crystallisation from isopropanol. The solid is filtered, washed with isopropanol and stove-dried at 50° C. under vacuum. 10.24 g of 2,3,4,6-tetra-O-benzyl-N-butyl-1-deoxynojirimycin of formula (VI) is obtained as a white solid with a yield of 44% from 2,3,4,6-tetra-O-benzyl-D-glucitol of formula (V), with a chemical purity, evaluated by HPLC, of 99.7% in A %.

Example 5

General Procedure for the Synthesis of 2,3,4,6-tetra-O-benzyl-N-butyl-1-deoxynojirimycin of Formula (VI)

In a 250 ml reactor under N$_2$, oxalyl chloride (8.8 g, 71 mmol) is dissolved in dichloromethane (29 ml), and the solution is cooled to −65° C. A solution of DMSO (7.5 g, 97 mmol) in dichloromethane (10 ml) is then added to the solution by dripping in about 40 minutes, followed by a solution of 2,3,4,6-tetra-O-benzyl-D-glucitol of formula (V) (10 g, 18 mmol) in dichloromethane (10 ml) in 1 h. At the end of the addition the reaction mixture is maintained at the same temperature under stirring for 30 minutes. The mixture is then treated with triethylamine (18.2 g, 182 mmol), added by dripping in 45 minutes. The mixture is then left to stand at 0° C. and treated with a 5.5% solution of NaOCl (131 ml), maintaining the temperature below 5° C. The phases are separated and the organic phase is maintained at 0° C. and washed sequentially with H$_2$O (50 ml) and 3M HCl (50 ml). The solution of 2,3,4,6-tetra-O-benzyl-D-xylo-hexo-5-ulose thus obtained is added in a 250 ml reactor containing a mixture of MeOH (40 ml), AcOH (15 g, 251 mol) and n-butylamine (13.2 g, 181 mol) at 0° C. At the end of the addition, the borane complex with an amine of formula (IX) or the borane complex with a pyridine of formula (X) (47 mmol, 2.6 moles per mole of the initial 2,3,4,6-tetra-O-benzyl-D-glucitol of formula (V)) is loaded at 0° C. The reaction mixture is maintained under stirring for 3 h at about 0° C., and then heated to about 20° C. After 15 hours under stirring at the same temperature, the end-of-reaction mixture is washed with a 3M HCl solution (40 ml). The phases are separated and the organic phase is washed sequentially with a 10% solution of K$_2$CO$_3$ (36 ml) and a 5% aqueous solution of NaCl (36 ml), and then dried on Na$_2$SO$_4$. After filtration the solution is concentrated at low pressure, and the residue obtained is crystallized from IPA. The 2,3,4,6-tetra-O-benzyl-N-butyl-1-deoxynojirimycin of formula (VI) is obtained as a white solid, and the yields obtained from the 2,3,4,6-tetra-O-benzyl-D-glucitol of formula (V) with the various aminoborane reducing complexes of formula (IX) or (X) are reported in the table below.

| Reducing agent | Yield |
|---|---|
| t-BuNH$_2$•BH$_3$ | 27% |
| 2-methylpyridine•BH$_3$ | 40% |
| 5-ethyl-2-methylpyridine•BH$_3$ | 30% |
| Morpholine•BH$_3$ | 65% |
| Me$_2$NH•BH$_3$ | 64% |

The invention claimed is:
1. A process for preparing a compound of formula (VI), or a salt thereof,

wherein
X is H or an alcohol protecting group selected from the group consisting of formyl, acetyl, chloroacetyl, trifluoroacetyl, benzoyl, allyl, propargyl, benzyl, p-methoxybenzyl, p-halobenzyl, 2,6-dihalobenzyl, and silyl ether; and
R is H, a C$_1$-C$_6$ alkyl group which is unsubstituted or substituted with one to three substituents independently selected from halogen and hydroxyl, or an amino protecting group selected from the group consisting of benzyl, benzyloxycarbonyl, tert-butyloxycarbonyl, 9-fluorenylmethyl, 2-chloro-3-indenylmethyl, 2,2,2-trichloroethyl, 2-chloroethyl, 2-adamantyl, 8-quinolyl, 4-methylsulfinylbenzyl, 2-methylthioethyl, 4-azidobenzyl, and N'-phenylaminothiocarbonyl;
comprising performing a reductive amination reaction of a dicarbonyl compound of formula (VII) at a temperature ranging from 0° C. to 30° C., wherein X is as defined above,

with an amine of formula (VIII), or a salt thereof,

wherein R is as defined above, in the presence of a reducing agent selected from a borane complex with an amine of formula (IX) or a borane complex with a pyridine of formula (X)

BH$_3$·NY$_3$, (IX)

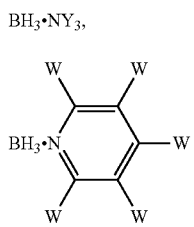
(X)

wherein each of substituents Y, being the same or different, is H, or a C$_1$-C$_6$ alkyl which is unsubstituted or substituted with one to three substituents independently selected from halogen and hydroxyl, or an aryl group which is unsubstituted or substituted by one to three substituents independently selected from the group consisting of a C$_1$-C$_4$ alkyl which is unsubstituted or substituted by one to three halogen atoms, hydroxyl, C$_1$-C$_4$ alkoxy, halogen, cyano, and nitro, or two of Y, taken together with the nitrogen atom to which they are linked, form a C$_5$-C$_6$ cycloalkyl ring optionally containing an oxygen atom or an =NRa group, wherein Ra is hydrogen, an amino protecting group selected from the group consisting of benzyl, benzyloxycarbonyl, tert-butyloxycarbonyl, 9-fluorenylmethyl, 2-chloro-3-indenylmethyl, 2,2,2-trichloroethyl, 2-chloroethyl, 2-adamantyl, 8-quinolyl, 4-methylsulfinylbenzyl, 2-methylthioethyl, 4-azidobenzyl, and N'-phenylaminothiocarbonyl, or a C$_1$-C$_4$ alkyl group; and each of substituents W, being the same or different, is H, a C$_1$-C$_6$ alkyl group which is unsubstituted or substituted with one to three substituents independently selected from halogen and hydroxyl, or a halogen atom; a solvent, and, isolating the compound of formula (VI) or a salt thereof.

2. The process according to claim 1, wherein a reducing agent is selected from a borane complex with an amine of formula (IX) or a borane complex with a pyridine of formula (X), wherein in the amine NY$_3$ one or two of Y, which may be the same or different, is a C$_1$-C$_4$ alkyl group, the remaining one or two of Y being hydrogen; or two of Y, taken together with the nitrogen atom to which they are linked, form a C$_5$-C$_6$ cycloalkyl ring, optionally containing an oxygen atom or an =NRa group, wherein Ra is hydrogen, an amino-protecting group selected from the group consisting of benzyl, benzyloxycarbonyl, tert-butyloxycarbonyl, 9-fluorenylmethyl, 2-chloro-3-indenylmethyl, 2,2,2-trichloroethyl, 2-chloroethyl, 2-adamantyl, 8-quinolyl, 4-methylsulfinylbenzyl, 2-methylthioethyl, 4-azidobenzyl, and N'-phenylaminothiocarbonyl, or a C$_1$-C$_4$ alkyl group, the remaining one of Y being hydrogen; and in the borane complex with a pyridine of formula (X), the pyridine ring is unsubstituted or substituted by one to three substituents independently chosen from a halogen atom and a C$_1$-C$_6$ alkyl group.

3. The process according to claim 1, wherein a reducing agent is selected from a borane complex with an amine of formula (IX) or a borane complex with a pyridine of formula (X), wherein in the amine NY$_3$ one or two of Y, which may be the same or different, is a C$_1$-C$_4$ alkyl group, the remaining one or two of Y being hydrogen; or two of Y, taken together with the nitrogen atom to which they are linked, form a morpholine, piperidine or piperazine ring, the remaining one of Y being hydrogen; and in the borane complex with a pyridine of formula (X), the pyridine ring is unsubstituted or substituted by one or two C$_1$-C$_4$ alkyl groups, which may be the same or different.

4. The process according to claim 1, wherein in a borane complex with an amine of formula (IX), one or two of Y is a C$_1$-C$_4$ alkyl group, which may be the same or different, the remaining one or two of Y being hydrogen; or two of Y, taken together with the nitrogen atom to which they are linked, form morpholine, piperidine or piperazine ring, the remaining one of Y being hydrogen.

5. The process according to claim 1, wherein in a borane complex with a pyridine of formula (X), the pyridine ring is substituted by one or two C$_1$-C$_4$ alkyl groups, which may be the same or different.

6. The process according to claim 1, wherein the reducing agent is a borane complex with an amine of formula (IX), wherein the corresponding amine of formula (IXa)

NY$_3$ (IXa)

is a secondary amine of formula (IXa), wherein one Y group is H and the remaining two Y groups, taken together with the nitrogen atom to which they are linked, form a morpholine ring.

7. The process according to claim 1, wherein the reductive amination reaction is carried out by treating a dicarbonyl compound of formula (VII) with at least a stoichiometric amount of an amine of formula (VIII) and at least 2 moles of a reducing agent of formula (IX) or (X) per mole of compound of formula (VII).

8. The process according to claim 1, further comprising preparing the reducing agent of formula (IX) or (X) in situ.

9. The process according to claim 1, wherein the reaction is carried out at 25° C.

10. The process according to claim 1, wherein the pH of the reaction mixture ranges between 8 and 4.

11. The process according to claim 1, further comprising alkylating a compound of formula (VI), wherein R is hydrogen and each of X is an alcohol protecting group selected from the group consisting of formyl, acetyl, chloroacetyl, trifluoroacetyl, benzoyl, allyl, propargyl, benzyl, p-methoxybenzyl, p-halobenzyl, 2,6-dihalobenzyl, and silyl ether, to obtain a corresponding alkylated compound of formula (VI), wherein R is butyl, and removing the alcohol protecting groups to obtain the compound of formula (I) miglustat,

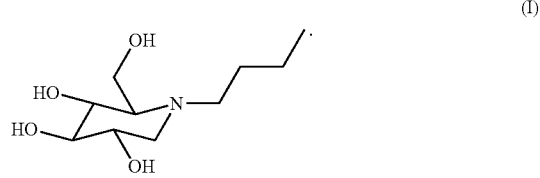
(I)

12. The process according to claim 1, wherein the solvent is selected from the group consisting of a dipolar aprotic solvent, an ether solvent, a chlorinated solvent, an ester solvent, a polar aprotic solvent, water, and mixtures thereof.

13. The process according to claim 1, wherein R is selected from the group consisting of methyl, ethyl, propyl, isopropyl, butyl, isobutyl, and tert-butyl.

14. The process according to claim 13, wherein R is butyl.

15. The process according to claim 14, wherein X is hydrogen.

16. The process according to claim 14, wherein X is benzyl.

17. The process according to claim 1, further comprising removing the X groups from the compound of formula (VI) when X is other than hydrogen, and optionally isolating the resulting compound.

\* \* \* \* \*

UNITED STATES PATENT AND TRADEMARK OFFICE
CERTIFICATE OF CORRECTION

| | | |
|---|---|---|
| PATENT NO. | : 9,708,263 B2 | |
| APPLICATION NO. | : 15/098647 | |
| DATED | : July 18, 2017 | |
| INVENTOR(S) | : Andrea Malvestiti | |

It is certified that error appears in the above-identified patent and that said Letters Patent is hereby corrected as shown below:

On the Title Page

The Assignee's city should be changed from "Baranzata (IT)" to --Baranzate (IT)--

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*